United States Patent [19]
Isogai et al.

[11] Patent Number: 5,940,165
[45] Date of Patent: Aug. 17, 1999

[54] OPHTHALMIC APPARATUS

[75] Inventors: Naoki Isogai, Nishio; Noriji Kawai, Gamagori, both of Japan

[73] Assignee: Nidek Co., Ltd., Gamagori, Japan

[21] Appl. No.: 09/015,630

[22] Filed: Jan. 29, 1998

[30] Foreign Application Priority Data

Jan. 31, 1997 [JP] Japan ................................. 9-033344

[51] Int. Cl.[6] .................................................. A61B 3/14
[52] U.S. Cl. ................................................... 351/208
[58] Field of Search ................................. 351/205, 204, 351/208, 211, 212, 237, 246; 606/166, 4, 10

[56] References Cited

U.S. PATENT DOCUMENTS 5,406,076  4/1995  Mimura et al. .
5,463,430  10/1995  Isogai et al. .

FOREIGN PATENT DOCUMENTS

A 62-57534  3/1987  Japan .
B2 1-19896  4/1989  Japan .
Y2 6-12729  4/1994  Japan .
A 8-107881  4/1996  Japan .

OTHER PUBLICATIONS

U.S. Patent Application entitled, "Ophthalmic Apparatus" which corresponds to JP–A 8–334591, filed Dec. 1, 1997 in Japan.

*Primary Examiner*—George Manuel
*Attorney, Agent, or Firm*—Oliff & Berridge, PLC

[57] ABSTRACT

An ophthalmic apparatus including measurement device for measuring visual performance of an eye to be examined and alignment device for aligning the measurement device relative to the eye, the apparatus comprising condition setting device for setting a finish condition capable of finishing measurement, which indicates that the necessary measured result is obtained, judging device for judging whether the result obtained by the measurement device satisfies the finish condition or not, and informing device for informing an operator that the finish condition is satisfied at the time when it is judged by the judging device.

30 Claims, 5 Drawing Sheets

OPHTHALMIC APPARATUS

BACKGROUND OF THE INVENTION

1. Field of the Invention

The present invention relates to an ophthalmic apparatus for measuring visual performance of an eye, and more particularly, to the apparatus for performing measurement of visual performance such as corneal curvature, refractive power and the like many times.

2. Description of Related Art

An ophthalmic apparatus, such as a refractive power measurement apparatus or a corneal curvature measurement apparatus, performs measurement by aligning the apparatus to be predetermined positional relationships relative to an eye to be examined. This kind of apparatus usually measures the same eye many times. For example, in the case of measuring refractive power, the measured result tends to change caused by accommodation or the like, therefore, the measurement should be performed many times, its result is utilized for calculating the average data, or if measured value is to be stable, then the measurement is stopped, the data at the time is adopted.

Also, a compound apparatus having plural functions for measurement such as refractive power measurement and corneal curvature measurement is well known, referring to this apparatus, measurement by respective functions is performed in order with the same eye. In this case, each measurement is performed many times, the averaged data is calculated among result, or if measured value is to be stable, then the measurement is stopped, the data at the time is adopted.

However, in the case that the averaged data is calculated by performing measurement many times as described above, an operator should count how many times measurement is performed, or should judge whether inspection is to be stopped by confirming the measured value which is displayed, therefore these works takes much time and make the operator be troubled. Furthermore, there is such disadvantage that measured result depends on operators.

On the other side, in the case that the data which is obtained at the time when data becomes stable, the operator had to memorize all measured result per each measurement, or to confirm measured result, which is displayed, one by one, therefore, there is such disadvantage that the operator can not concentrate the measurement.

In addition, referring to the compound apparatus having plural functions for measurement, if measurement of one function is finished, but measurement of the other function is not finished, then the measurement of one function, which has finished, is performed repeatedly, therefore, there is disadvantage that whole measurement takes much time. If it takes much time, then the eye becomes tired and accuracy of measured result to be obtained is influenced thereby.

SUMMARY OF THE INVENTION

The present invention has been made in view of the above circumstances and has an object to overcome the above problems and to provide an ophthalmic apparatus, which can make an operator concentrate measurement without counting the number of times of measurement and without judging whether measurement is finished or not, and also which can obtain highly accurate measured result without depending on each operator's judgement.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic apparatus including measurement means for measuring visual performance of an eye to be examined and alignment means for aligning the measurement means relative to the eye, the apparatus comprises condition setting means for setting a finish condition capable of finishing measurement, which indicates that the necessary measured result is obtained, judging means for judging whether the result obtained by the measurement means satisfies the finish condition or not, and informing means for informing an operator that the finish condition is satisfied at the time when it is judged by the judging means.

In another aspect of the present invention, an ophthalmic apparatus including refractive power measuring optical system and corneal curvature measuring optical system, the apparatus comprises measurement finish condition setting means for setting finish condition which indicates that the measurement is finished by obtaining the predetermined measured data, and judging means for judging whether the measurement finish condition set by the measurement finish condition setting means is satisfied or not, whereby execution of measurement is stopped at the time when it is judged by the judging means that the measurement finish condition is satisfied.

According to the present invention, the operator can concentrate the measurement since it is informed of the operator that the apparatus satisfies the predetermined finish condition, therefore highly accurate measured result can be obtained efficiency.

Also, difference of judgement of the measurement finish, which depends on an operator, is removed, therefore, reliability of the measured result to be obtained is improved without relating to difference of an operator.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
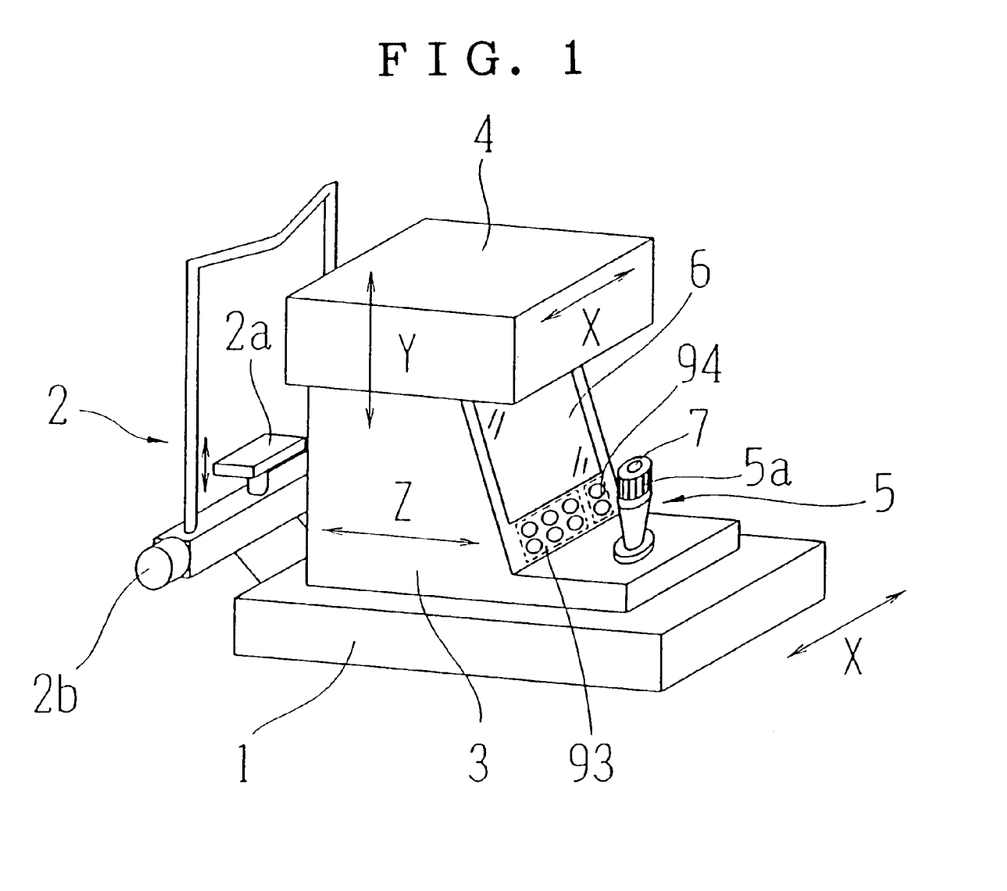
FIG. 1 is an overview of an apparatus of the preferred embodiment of the present invention.

A detailed description of one preferred embodiment of an ophthalmic apparatus embodying the present invention will now be given referring to the accompanying drawings by making a point of an ophthalmic apparatus having functions for measurement both of a refractive power and a corneal curvature as an example. FIG. 1 shows an overview of the apparatus of the preferred embodiment of the present invention. Reference numeral 1 is a base to which a face support unit 2 which is utilized for fixing a face of an examinee is fixed. The face support unit 2 holds a chin rest 2a so that it may move up and down, and the chin rest 2a can be made to move up and down by rotating a chin rest knob 2b, thereby a height position of an eye to be examined can be adjusted.

3 is a body, 4 is a measuring part which holds optical systems mentioned below. 5 is a joystick which is utilized for moving the body 3 and the measuring part 4, the body 3 moves and slides on a horizontal surface of the base 1 in Z-direction (forward and backward directions) and X-direction (a lateral direction) by operating the joystick 5, and the measuring part 4 moves in Y-direction (a vertical direction) by operating a rotation knob 5a, which is provided for a joystick 5, relative to the body 3 (concerning mechanism of joystick, see U.S. Pat. No. 5,406,076 corresponding to Japanese Patent Laid Open No.HEI6-7292). In addition, the measuring part 4 is configured so as to move to XY directions relative to the body 3 in order to cope with the automatic alignment (mentioned below).

Reference numeral 6 is TV monitor which displays an image of the eye and information to be informed of the operator. 7 is a starting switch for measurement.

Figure 2:
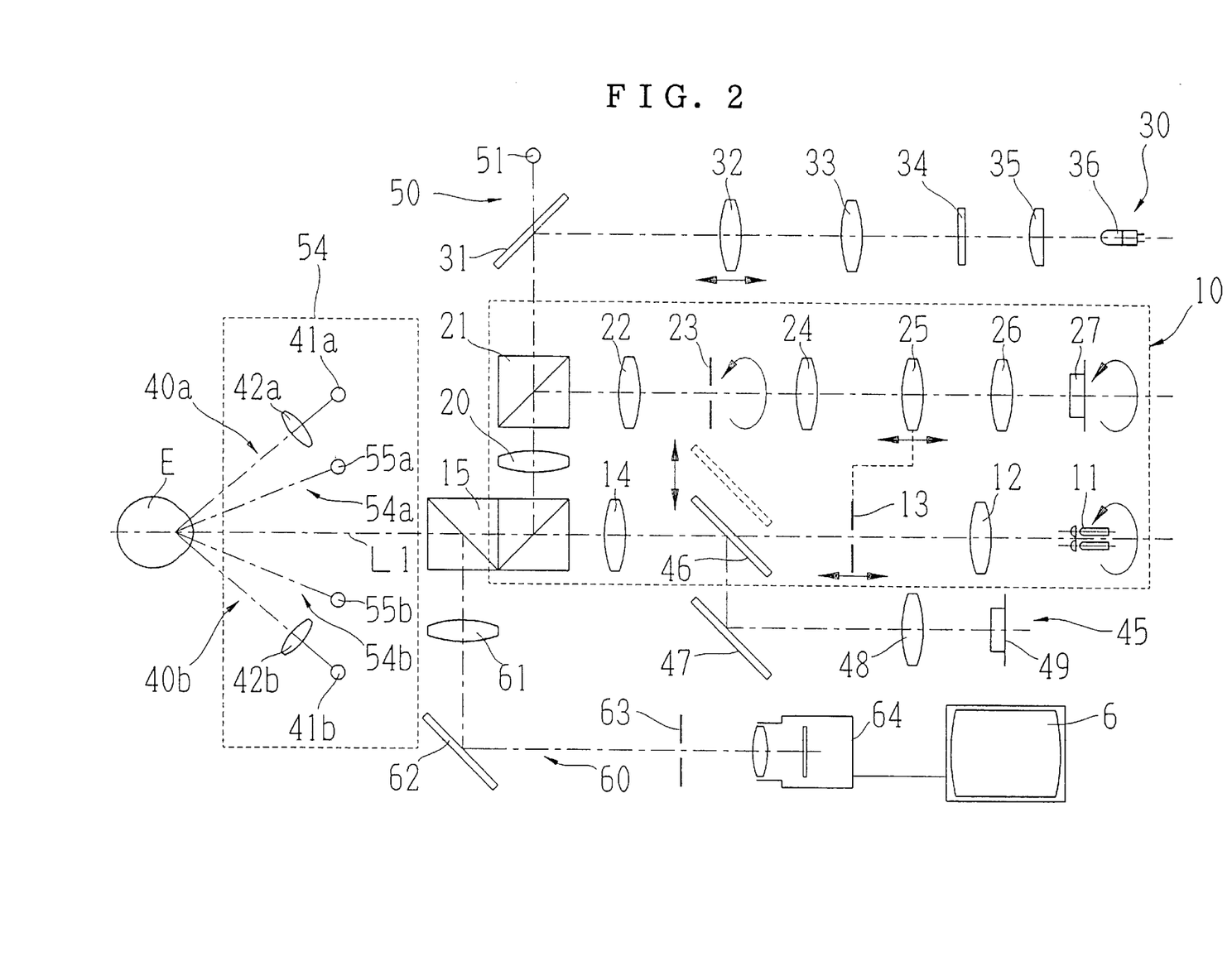
FIG. 2 is a view showing a schematic arrangement of an optical system of the apparatus of the preferred embodiment of the present invention.

Next, a schematic construction of the apparatus will be described referring to FIG. 2.

Reference numeral 10 denotes a refractive power measuring optical system. 11 is two light sources for measurement having wavelength of infrared range, which is disposed so as to rotate with the center at an optical axis L1. 12 is a condenser lens, the light sources 11s are positioned at a focusing point in front of thereat. 13 is a target plate for measurement having a target for measurement (a spot aperture), which can move so as to be disposed at a conjugate position relative to a fundus of the eye E. 14 is a projecting lens, 15 is a beam splitter, 20 is an objective lens, 21 is a beam splitter, 22 and 24 are relay lenses, 23 is a corneal reflection eliminating mask, being belt shaped, which is disposed at a conjugate position relative to a cornea of the eye E so that it may rotate with the center at the optical axis being synchronized with the light sources 11s, 25 is a movable lens which moves together with the target plate 13, and 26 is a focusing lens. 27 is a photo-detector for measurement, which rotates with the center at the optical axis being synchronized with the light sources 11s and the corneal reflection eliminating mask 24.

Reference numeral 30 denotes a fixation target optical system. 31 is a half mirror, 32 is a first relay lens capable of moving on the optical axis and fogs the eye E by moving on the optical axis. 33 is a second relay lens, 34 is a fixation target disposed at a focusing position of the second relay lens 33, 35 is a condenser lens, and 36 is an illumination lamp.

Reference numerals 40a to 40d are four pairs of target projecting optical systems for measuring corneal curvature, which are disposed on the same circumference with the center at the measuring optical axis L1. The target projecting optical systems 40a and 40b are disposed in a horizontal direction of the apparatus, and the target projecting optical systems 40c and 40d (not shown in FIG. 2) are disposed in a vertical direction of the apparatus, so that respective projecting optical axes may intersect at the predetermined angle relative to the measuring optical axis L1. 41a to 41d are point light sources which emit infrared light, and 42a to 42d are collimating lenses which project a target of infinite distance onto the eye E.

Reference numeral 45 is a target detecting optical system for detecting a target for measuring corneal curvature, which includes a mirror 46 which is inserted in the measuring optical axis L1 when measuring corneal curvature and, a mirror 47, a focusing lens 48, and a two-dimensional photo-detector 49.

Reference numeral 50 denotes a target projecting optical system for projecting an alignment target from a visual axis direction. Light from a point light source 51 which emits infrared light is made to be parallel luminous flux by the objective lens 20 via the half mirror 31 and the beam splitter 21, and is reflected by the beam splitter 15, then projects the target from a front of the eye E along the measuring optical axis L1.

Reference numeral 54 is a target projecting optical system for projecting an alignment target for detecting the working distance. The target projecting optical system 54 shares the target projecting optical systems 40a and 40b which are arranged in a horizontal direction among above mentioned target projecting optical systems for measuring corneal curvature, further it includes target projecting optical systems 54a and 54b which are arranged to be symmetry with forming the predetermined angle (its angle is smaller than the target projecting optical systems 40a and 40b) with respect to a horizontal direction with putting the measuring optical axis L1 therebetween. The target projecting optical system 54a and 54b includes point light sources 55a and 55b which emit infrared light and project the finite target onto the eye E.

Reference numeral 60 denotes an observing optical system. Image of an anterior part of the eye illuminated by an illumination light source, which is not shown, is reflected at the beam splitter 15, then is photographed by CCD camera 64 via an objective lens 61, a mirror 62 and a telecentric diaphragm 63. Also, the observing optical system 60 serves as a detecting optical system of an alignment target which is projected onto the eye E.

Figure 3:
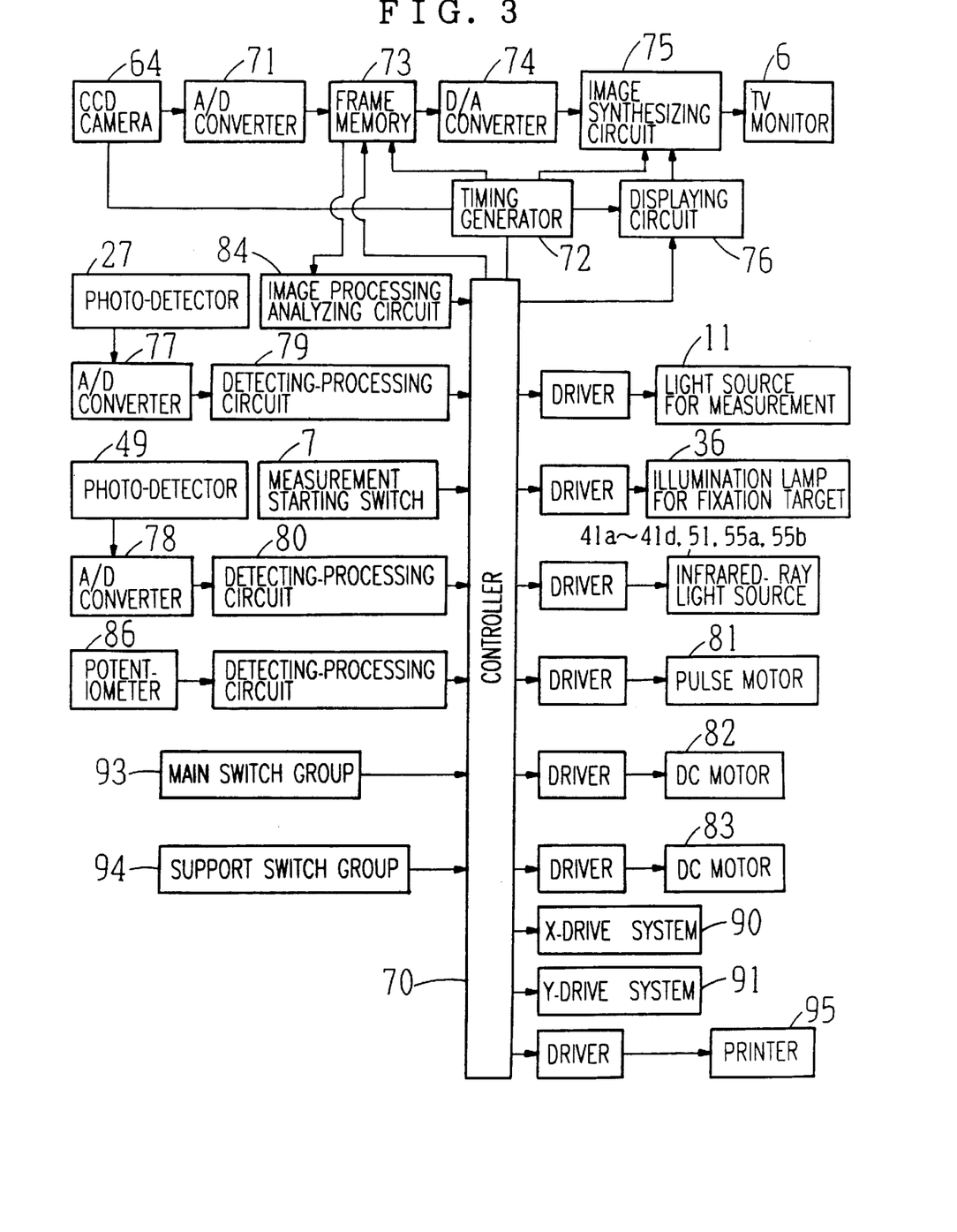
FIG. 3 is a view showing an important construction of a controlling system of the apparatus of the preferred embodiment of the present invention.

Next, the important construction of the controlling system of the apparatus will be described referring to FIG. 3. A video signal from CCD camera 64 is digitized by A/D converter 71, then is captured by a frame memory 73 being synchronized with a signal from a timing generator 72. The image captured by the frame memory 73 is displayed on TV monitor 6 in real-time via D/A converter 74 and an image synthesizing circuit 75.

Reference 76 is a display circuit for generating reticle marks, graphics, characters information and the like, which are displayed on TV monitor 6 (reticle marks may be made optically). A signal from the display circuit 76 is synthesized with a picture signal from CCD camera 64 by the image synthesizing circuit 75 so as to be displayed on TV monitor 6. 84 is an image processing-analyzing circuit for detecting the alignment target image by analyzing the image captured by the frame memory 73, and a controller 70 obtains coordinates of the target image based on a signal from the image processing-analyzing circuit 84. In addition, respective signals from the photo-detector 27 and 49 are digitized by A/D converters 77 and 78, and the predetermined process is given to the signals by respective detecting-processing circuits 79 and 80, then are inputted into the controller 70.

Reference numeral 90 is X-drive system for driving the measuring part 4 in X-direction relative to the body 3, 91 is Y-drive system for driving the same in Y-direction, and respective drive systems consist of a slide mechanism, a motor and a driving circuit for a motor and the like. Also, 81 is a pulse motor for driving the first relay lens 32, 82 is DC motor for driving the target plate 13 and the movable lens 25, 83 is DC motor for driving the mirror 46. 86 is a potentiometer for detecting amount of movement of the movable lens 25 and the target plate 13. The predetermined process is given to the value detected by the potentiometer 86, and the value is inputted into the controller 70.

Reference numeral 93 is a main switch group which includes a change-over switch for selecting that automatic shot measurement which generates a trigger signal automatically and then performs measurement is performed or not, an alignment mode change-over switch for selecting a manual alignment and an automatic alignment, a measurement mode change-over switch for selecting the measurement of refractive power and that of corneal curvature to be performed continuously or independently, and the like. 94 is a support switch group which includes switches for changing or inputting several kinds of condition settings.

Next, the operation of the apparatus of the preferred embodiment having such architecture as described above hereinafter. In following, such cases are will be described that the automatic alignment mode, the automatic shot measurement, and the continuous measurement of refractive power and corneal curvature are selected (see FIG. 4).

The operator adjusts a position of the examinee's face on the face support unit 2 so as to fix the eye E. Then, the operator performs alignment roughly by operating the joystick 5 and the rotation knob 5a with observing an image 100 of the anterior part of the eye, a reticle mark 101, alignment target images 102, 103a–103d (see FIG. 5), so that the target image 102 of the point light source 51, which is formed by corneal reflection of the center thereof, may be made for the reticle mark 101.

Figure 5:
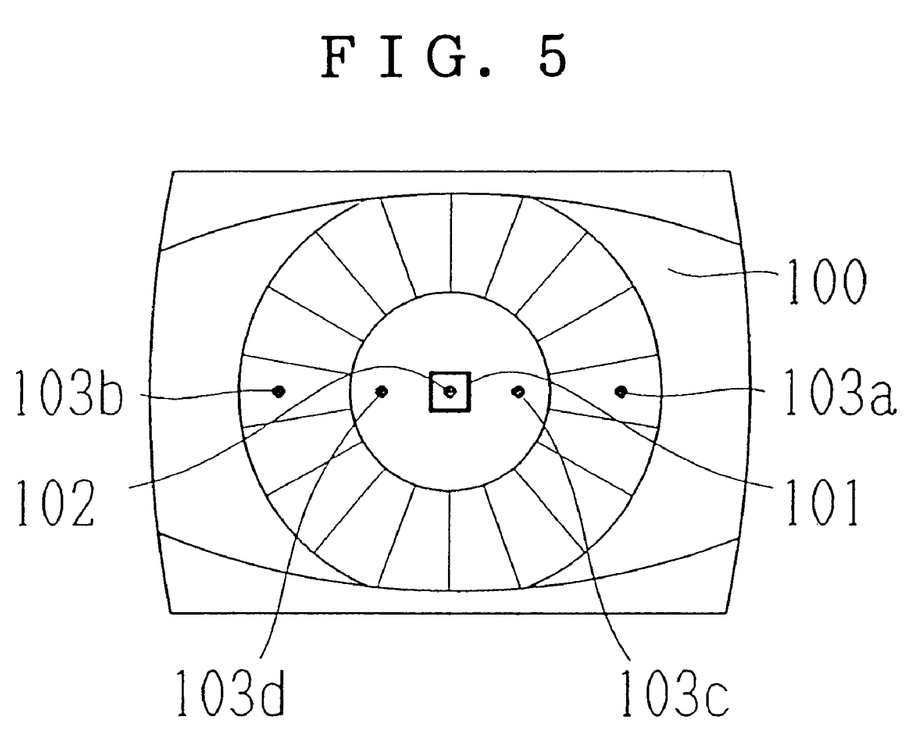
FIG. 5 is a view showing an example of an image which is displayed on TV monitor at the time of alignment.

Once five target images are caught by CCD camera 64, the controller 70 extracts the target image 102 of the point light source 51 based on a signal from the image processing-analyzing circuit 84, thereby obtains a deviation distance in XY directions. Then, the measuring part 4 is made to move by driving X-drive system 90 and the Y-drive system 91 based on the deviation distance, then the alignment in XY directions is completed so that the deviation distance may be within the predetermined permissible range.

The alignment in XY directions is completed by the automatic alignment, then alignment adjustment of working distance is performed by causing the measuring part 4 to move toward and away relative to the eye E by operating the joystick 5. The apparatus detects target images formed by the target projecting optical systems 40a, 40b, 54a and 54b, thereby judges the alignment condition of the working distance. Detection of the working distance is performed by comparing the distance (height of image) between the target image formed by the target projecting optical systems 40a and 40b and the target image formed by the target projecting optical systems 54a and 54b. In this case such characteristic is utilized that, in the case that the corneal reflex is formed by an infinite-distance light source and a finite-distance light source, even if the working distance changes, then the height of image formed by the infinite-distance light source does not change, however, the height of image formed by the finite-distance light source changes (details of the relationships is mentioned in U.S. Pat. No. 5,463,430 corresponding to Japanese Patent Laid-Open No.HEI6-46999).

Based on judgement of the alignment condition in Z direction (the working distance) and XY directions, the controller 70 starts measurement by generating a trigger signal automatically when the predetermined alignment is completed (performing the automatic shot measurement). In the preferred embodiment, firstly, the measurement of corneal curvature is performed. The controller 70 drives DC motor 83, thereby the mirror 46 is inserted in the measuring optical axis L1, and the controller 70 causes the point light sources 51, 55a and 55b used for alignment to be turned off, and causes the point light sources 41a to 41d used for measuring corneal curvature to be turned on. Light reflexes by the point light sources 41a to 41d are transmitted into the photo-detector 49 by the mirror 46 and 47 and the like. Based on a signal from the photo-detector 49, the controller 70 calculates corneal curvature. As mentioned in Japanese Patent Publication No.HEI1-19896 (KOKOKU), if three target images are detected, then corneal curvature can be calculated.

Figure 4:
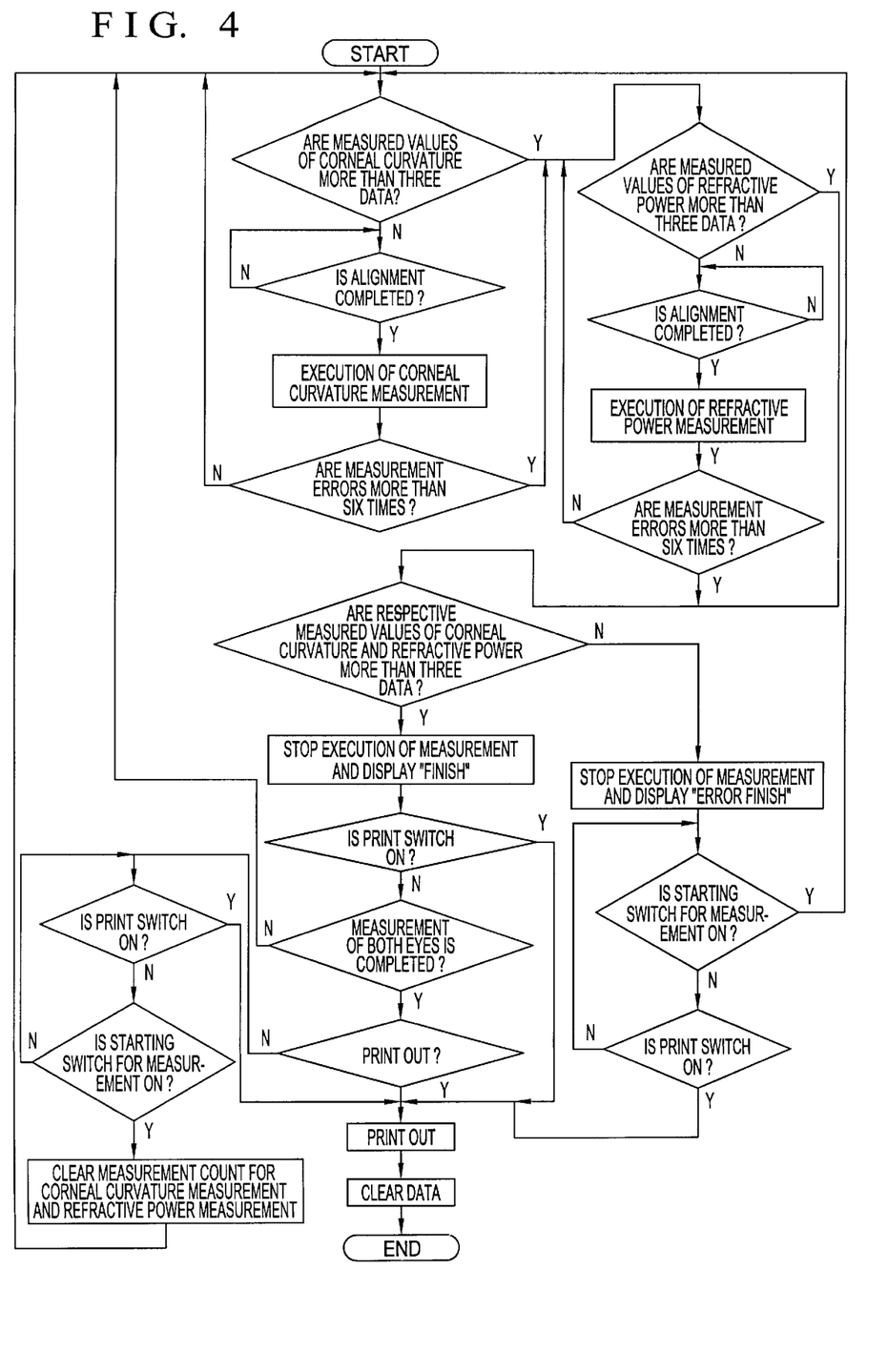
FIG. 4 is a flowchart for describing the measurement process.

In the measurement of corneal curvature, if the predetermined number (for example, three) or more of the measured values exclusive of the measurement errors are obtained, or the measurement errors become more than or equal to the predetermined number (for example, six), then it is proceeded to the measurement of refractive power.

If the predetermined number (three) or more measured values exclusive of the measurement errors are obtained (or measurement errors become the predetermined number (six) or more), the controller 70 causes the mirror 46 to be evacuated from the optical axis L1, then starts the measurement of refractive power automatically. The measurement luminous flux from the light sources 11s for measurement is converged at the position close to the cornea of the eye E via the condenser lens 12, the target plate 13, the projecting lens 14 and the beam splitter 15, then is transmitted to the fundus of the eye E. The target image reflected at the fundus of the eye E forms an image on the photo-detector 27 by the focusing lens 26 after passing through the beam splitter 15, the objective lens 20, the beam splitter 21, and the relay lenses 22 and 24. In the case that the eye E has ametropia, the controller 70 drives DC motor 82, thereby causes the movable lens 25 as well as the target plate 13 to move to the conjugate position relative to the fundus of the eye E.

Next, the fixation target 34 and the fundus of the eye E are made to be conjugate position each other by moving the first relay lens 32, then are made to move so that appropriate amount of diopter may be fogged. Under the condition that the eye E is fogged, the light sources 11s for measurement, the corneal reflection eliminating mask 24 and the photo-detector 27 are made to rotate 180° around the optical axis. While rotating, the target plate 13 and the movable lens 25 move by a signal from the photo-detector 27, and the movement amount is detected by the potentiometer 86, thereby respective values of refractive power are calculated in respective meridian directions. The controller 70 obtains refractive power of the eye E by giving the predetermined process to the values of refractive power.

On the other side, in the case of the measurement of refractive power, if the predetermined number (for example, three) of measured values exclusive of the measurement errors is obtained, or the number of the measurement errors becomes the predetermined number (for example, six), then it is judged whether each of numbers of the measurement of corneal curvature and of the measurement of refractive power is more than or equal to the predetermined number (three) or not.

In the case that both measurement obtain the predetermined number (three) or more data respectively, then the controller 70 finishes the measurement by judging that the measurement finish condition is satisfied, and displays "FINISH" meaning measurement finish of one eye on TV monitor 6 (or the measurement finish of one eye may be informed of the operator by sound or the like). Thereby, the operator can understand simultaneously that measured result having the predetermined condition is obtained, without confirming the number of times of the measurement and the number of the measured values which is displayed.

On the other side, both measurement do not obtain the predetermined number (three) or more data respectively, or, either the measurement does not obtain the predetermined number (three) or more data, then the controller 70 stops the measurement, then displays "ERROR FINISH" on TV monitor 6 (or it is informed of the operator that the measured result having predetermined condition is not obtained by sound or the like). It is configured so that each number of times of the measurement of corneal curvature and that of refractive power (number of measured values which are obtained) may be always displayed on TV monitor 6, therefore the operator can understand the number of measured values by looking at it. In addition, in this case, it may be easier to understand by causing the one not satisfying the predetermined number, which is set, to be turned on and off, or to be reversed.

When "ERROR FINISH" is displayed on TV monitor 6, the operator removes a cause of the measurement error (an eyelid, an eyelash or the like). Then, the operator presses the starting switch 7 for measurement and performs the alignment so that the automatic shot measurement may be repeated. If the measurement is reopened, then the one not satisfying the predetermined number (three for each) either the measurement for corneal curvature or the measurement for refractive power is performed so that a deficiency may be obtained (so that both of them satisfy more than or equal to the predetermined number (three)). For example, relating to the measurement of corneal curvature, if only one data is deficient, then its measurement of corneal curvature is only performed to obtain one measured value. Relating to both measurement, if the predetermined number (three) or more measured values are obtained, then the controller 70 stops the measurement by judging that the measurement finish condition is satisfied and displays "FINISH" meaning measurement finish of one eye on TV monitor 6.

In the case that plural functions for measurement are executed, if the number of measurement errors is set, then respective measurement do not takes long time. Also, if there is a function of which the measurement is finished, then its measurement is not performed, however exclusive of its measurement is only performed, therefore, the whole measurement time can be shortened without performing the excessive measurement. Also, the function for measurement which is completed is not obstacle to the remaining function for measurement. Also, it is informed of the operator that the apparatus satisfies the predetermined measurement finish condition, therefore the operator can concentrate the measurement. Therefore, efficiency of the measurement is improved, thereby uncomfortableness of the eye E may be decreased and more accurate measurement can be possible.

When the measurement of one eye is finished, the measurement of the other eye is performed as the same way. Once the measured values both right and left eyes satisfy the predetermined measurement finish condition in the measurement of corneal curvature and refractive power, then the controller 70 finishes the measurement and sends the measured data to the printer 95 (or other peripheral device connected thereto, IC card and the like). It is, of course, possible to stop the measurement after the measurement of one eye and out put the measured data. In this case, an unillustrated print switch is to be depressed when "FINISH" is displayed. Such processes that calculates the average value or the median value by using the measured data obtained by performing measurement plural times are given to its data, then the processed data are outputted.

In above, the continuous measurement of refractive power and the corneal curvature is described, in the case that the independent mode for measuring independently is selected, if the apparatus judges that the predetermined measurement finish condition is satisfied, then "FINISH" is displayed, and if the predetermined number of measured values of both eyes (or one eye) are obtained, then the measurement is finished and the measured data are outputted.

In addition, in the case that the automatic alignment and the automatic shot measurement are not performed, the operator only needs for confirming the display "FINISH" (or sound) in order to understand whether the predetermined measurement finish condition is satisfied or not, therefore the operator can concentrate the alignment adjustment and the observation of the eye. Thereby, highly accurate measurement can be performed easily. In addition, in the case that the measurement is performed by pressing the starting switch 7 for measurement by the operator without using the automatic shot measurement, since the apparatus has such function, during the starting switch 7 for measurement is pressed, that performs the continuous measurement with remaining the amount of fogging of the eye E as the same with the preceding measurement in the case of the measurement of refractive power, therefore the measurement can be performed with high speed.

Judgement for the measurement finish condition of the same eye in above mentioned embodiment, may be performed based on stability (degree of dispersion of plural measured values being within a certain condition). In the case of the measurement of corneal curvature, for example, if each of a curvature R1 in a 1st principle meridian direction and a curvature R2 in a 2nd principle meridian direction deviates from the preceding measured value within a range less than or equal to the constant (for example, 0.04 mm), and more than or equal to the predetermined number (for example, three) of measured values are obtained, then the measurement is finished. Or, making a standard deviation a condition, an average of the predetermined number of measured values which are obtained and a standard deviation are calculated, then it is judged whether the standard deviation is less than or equal to the constant (for example, 0.04 mm). If the standard deviation is less than or equal to the constant (0.04 mm), then it is judged that measurement is finished with defining that the effective measured values are obtained. If the standard deviation is more than the constant (0.04 mm), then the measured value which is the most deviant from the average is eliminated, then additional measurement is performed. And the same calculation is repeated, then it is judged whether the measurement is finished or additional measurement is needed.

In the case of the measurement of refractive power, for example, if each of a value S (spherical power) and a value C (cylindrical power) deviates from the preceding measured value within a range less than or equal to the constant (for example, 0.12 D), and the predetermined number (for example, three) of measured values are obtained, then the measurement is finished. Accuracy of a value A (astigmatism axial angle) changes with depending on the value C, therefore, if the value C is more than or equal to the constant (for example, 0.5 D), then the effective measured value may be extracted by adding condition of the value A. In addition, a standard deviation may be as a condition, as the same as the measurement of corneal curvature.

As described above, if stability of measured value is added to the condition of the measurement finish, then highly accurate measured results are obtained. Particularly, in the case of the measurement of refractive power, there is the case that the fogging is not effective to some eyes with allowing the value S to change to be a plus direction by degrees then to become stable (often in hyperopia), therefore, it is convenience that stability of measured value is added to the condition.

In addition, respective measurement finish condition for the measurement of corneal curvature and the measurement of refractive power (a number of the measured values exclusive of the measurement errors, the standard value for confirming the stability and the like) and a number of the measurement errors and the like can be set at will by using switches provided for the support switch group 94. Further, such functions as a function for judging whether the measured values which satisfy the predetermined measurement finish condition, a function for informing of the operator that the measured values which satisfy (or does not satisfy) the predetermined measurement finish function by the display, sound or the like, a function for stopping the measurement when the measured value which satisfy the predetermined finish condition is obtained in the case of the continuous measurement, a function for stopping the measurement when the measurement errors become the predetermined number, and a function for outputting (printing out or the like) the measured data automatically when the measurement is finished by obtaining the measured values which satisfy the predetermined finish condition for both eyes (or one eye), and the like are configured so that effective or invalid may be selected by using switches provided for the support switch group 94. If the function for outputting (printing out or the like) the measured data automatically when the measurement is finished by obtaining the measured values which satisfy the predetermined finish condition for both eyes (or one eye) is made to be invalid, then it is capable of outputting by pressing a print switch not shown by confirming the measured value which is obtained by the operator, or capable of measuring by clearing the number of measured values which are obtained (without clearing the measured values) so that the measured values exclusive of measurement errors may be obtained, repeatedly. Above mentioned setting of measurement condition and a selection for a measurement function can be used according to the condition of the operator and the examinee.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. For example, it is very useful that the present invention is adopted for the apparatus of full-automatic type. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is the claimed is:

1. An ophthalmic apparatus including measurement means for measuring visual performance of an eye to be examined and alignment means for aligning said measurement means relative to the eye, the apparatus comprising:

setting means for setting the number of measured values to be necessitated;

judging means for counting the number of measured values exclusive of the number of measurement errors and/or measured values deviating from a predetermined standard, and judging whether the counted number of measured values satisfies the set number of measured values or not; and informing means for informing an operator that the counted number of measured values satisfies the set number of measured values at the time when it is judged by said judging means.

2. The ophthalmic apparatus according to claim 1, being an apparatus for measuring corneal curvature, wherein said predetermined standard is that dispersion of curvature values in a principal meridian direction is within predetermined range.

3. The ophthalmic apparatus according to claim 1, being an apparatus for measuring refractive power, wherein said predetermined standard is that dispersion of refractive power is within predetermined range.

4. The ophthalmic apparatus according to claim 1, further comprising:

informing means for informing the operator that the measurement errors reach to the predetermined number of time at the time when it is also judged by said judging means.

5. The ophthalmic apparatus according to claim 1, further comprising:

both eyes finish judging means for judging whether measurement of both right and left eyes is finished or not;

data outputting means for printing out measured data by said measurement means and/or sending out the same to another apparatus; and controlling means for causing said data outputting means to work, at the time when it is judged by said both eyes finish judging means that the measurement of both eyes is finished.

6. The ophthalmic apparatus according to claim 1, wherein said alignment means includes alignment detecting means for detecting alignment condition of said measurement means relative to the eye, and alignment judging means for judging whether the alignment condition detected by said alignment detecting means is within predetermined permissible range or not; and the apparatus further comprising:

measurement execution instruction means for instructing said measurement means to execute measurement continuously, at the time when it is judged by said alignment judging means that the alignment condition is within the predetermined permissible range; and measurement discontinuing means for discontinuing execution of the measurement by said measurement execution instruction means, at the time when it is judged by said judging means that the counted number of measured values satisfies the set number of measured values.

7. The ophthalmic apparatus according to claim 1, further comprising:

displaying means for displaying measured data and the number of the same.

8. The ophthalmic apparatus according to claim 1, further comprising:

data outputting means for outputting measured data, at the time when it is judged by said judging means that the counted number of measured values satisfies the set number of measured values.

9. An ophthalmic apparatus including measurement means for measuring visual performance of an eye to be examined and alignment means for aligning said measurement means relative to the eye, the apparatus comprising:

setting means for setting the number of measured values to be necessitated;

judging means for counting the number of measured values exclusive of the number of measurement errors and/or measured values deviating from a predetermined standard, and judging whether the counted number of measured values satisfies the set number of measured values or not, and controlling means for continuously executing measurement performed by said measurement means in response to a measurement starting signal, and discontinuing execution of continuous measurement at the time when it is judged by said judging means that the counted number of measured values satisfies the set number of measured values.

10. The ophthalmic apparatus according to claim 9, wherein said controlling means discontinues the execution of continuous measurement, at the time when it is also judged by said judging means that the measurement errors reach to the predetermined number of time.

11. The ophthalmic apparatus according to claim 9, further comprising:

informing means for informing an operator that the counted number of measured values satisfies the set number of measured values at the time when it is judged by said judging means.

12. The ophthalmic apparatus according to claim 9, further comprising: both eyes finish judging means for judging whether measurement of both right and left eyes is finished or not;

data outputting means for printing out measured data by said measurement means and/or sending out the same to another apparatus; and controlling means for causing said data outputting means to work, at the time when it is judged by said both eyes finish judging means that the measurement of both eyes is finished.

13. The ophthalmic apparatus according to claim 9, further comprising:

displaying means for displaying measured data and the number of the same.

14. The ophthalmic apparatus according to claim 9, further comprising:

data outputting means for outputting measured data, at the time when it is judged by said judging means that the counted number of measured values satisfies the set number of measured values.

15. An ophthalmic apparatus including measurement means for measuring visual performance of an eve to be examined and alignment means for aligning said measurement means relative to the eye, the apparatus comprising:

setting means for setting the number of measured values to be necessitated, error number setting means for setting the number of measurement errors for discontinuing measurement;

judging means for counting the number of measured values, judging whether the counted number of measured values satisfies the set number of measured values or not, counting the number of measurement errors, and judging whether the counted number of measurement errors satisfies the set number of measurement errors or not; and controlling means for continuously executing measurement performed by said measurement means in response to a measurement starting signal, and discontinuing execution of continuous measurement at the time when it is judged by said judging means that the counted number of measured values satisfies the set number of measured values or the counted number of measurement errors satisfies the set number of measurement errors.

16. The ophthalmic apparatus according to claim 15, further comprising:

both eyes finish judging means for judging whether measurement of both right and left eyes is finished or not;

data outputting means for printing out measured data by said measurement means and/or sending out the same to another apparatus; and controlling means for causing said data outputting means to work, at the time when it is judged by said both eyes finish judging means that the measurement of both eyes is finished.

17. The ophthalmic apparatus according to claim 15, further comprising:

informing means for informing an operator that the counted number of measured values satisfies the set number of measured values and/or the counted number of measurement errors satisfies the set number of measurement errors at the time when it is judged by said judging means.

18. The ophthalmic apparatus according to claim 15, further comprising:

displaying means for displaying measured data and the number of the same.

19. The ophthalmic apparatus according to claim 15, further comprising:

data outputting means for outputting measured data, at the time when it is judged by said judging means that the counted number of measured values satisfies the set number of measured values.

20. An ophthalmic apparatus including first measurement means for measuring first performance of an eye to be examined, second measurement means for measuring second performance of the eye, and alignment means for aligning said first and second measurement means relative to the eye, the apparatus comprising:

setting means for setting the number of measured values to be necessitated with regard to said first and second measurement means;

judging means for counting the number of measured values exclusive of the number of measurement errors and/or measured values deviating from a predetermined standard, and judging whether the counted number of measured values satisfies the set number of measured values or not, with regard to said first and second measurement means separately;

measurement starting signal generating means for generating a measurement starting signal which causes said first and second measurement means to execute measurement in order; and controlling means for controlling measurement of said first and second measurement means so that the measurement of which the counted number of measured values satisfies the set number of measured values may be finished, and the measurement of which the counted number of measured values does not satisfy the set number of measured values may be performed, in the case that it is judged by said judging means that either of the counted number of measured values of those performance satisfies the set number of measured values by executing measurement by said measurement starting signal.

21. The ophthalmic apparatus according to claim 20, wherein said setting means includes first and second setting means for setting the number of measured values to be necessitated of said first and second measurement means separately.

22. The ophthalmic apparatus according to claim 20, wherein said first measurement means includes a refractive power measuring optical system, and said second measurement means includes a corneal curvature measuring optical system.

23. The ophthalmic apparatus according to claim 22, further comprising:

independent mode selecting means for performing independently either measurement of refractive power by said refractive power measuring optical system or measurement of corneal curvature by said corneal curvature measuring optical system.

24. The ophthalmic apparatus according to claim 20, further comprising:

measurement execution stopping means for stopping execution of measurement, at the time when the measurement errors reach to the predetermined number of time.

25. The ophthalmic apparatus according to claim 24, further comprising:

informing means for informing an operator that said measurement execution stopping means works, at the time when it does.

26. The ophthalmic apparatus according to claim 20, wherein said first measurement means includes a corneal curvature measuring optical system, said second measurement means includes a refractive power measuring optical system and said predetermined standard is that each dispersion of curvature values in a first principal meridian direction and a second principal meridian direction is within predetermined range in the case of measurement of corneal curvature, and it is that each dispersion of spherical power and cylindrical power is within predetermined range in the case of measurement of refractive power.

27. The ophthalmic apparatus according to claim 20, further comprising:

both eyes finish judging means for judging whether measurement of both right and left eyes is finished or not;

data outputting means for printing out measured data by said measurement means and/or sending out the same to another apparatus; and controlling means for causing said data outputting means to work, at the time when it is judged by said both eye finish judging means that the measurement of both eyes is finished.

28. The ophthalmic apparatus according to claim 20, further comprising:

informing means for informing an operator that the counted number of measured values by said first and second measurement means satisfies the set number of measured values at the time when it is judged by said judging means.

29. The ophthalmic apparatus according to claim 20, further comprising:

displaying means for displaying measured data and the number of the same.

30. The ophthalmic apparatus according to claim 20, further comprising:

data outputting means for outputting measured data, at the time when it is judged by said judging means that the counted number of measured values by said first and second measurement means satisfies the set number of measured values.

* * * * *